United States Patent
Kim et al.

(10) Patent No.: US 9,248,152 B2
(45) Date of Patent: Feb. 2, 2016

(54) HUMAN NEURAL STEM CELLS EXPRESSING HUMAN CHOLINE ACETYLTRANSFERASE, AND USE THEREOF

(75) Inventors: Yun-Bae Kim, Daejeon (KR); Seung Up Kim, Suwon-si (KR)

(73) Assignee: CHUNGBUK NATIONAL UNIVERSITY INDUSTRY ACADEMIC COOPERATION FOUNDATION, Chungcheongbuk-Do (KR)

( * ) Notice: Subject to any disclaimer, the term of this patent is extended or adjusted under 35 U.S.C. 154(b) by 69 days.

(21) Appl. No.: 13/878,346

(22) PCT Filed: Jul. 4, 2011

(86) PCT No.: PCT/KR2011/004886
§ 371 (c)(1),
(2), (4) Date: Apr. 8, 2013

(87) PCT Pub. No.: WO2012/046946
PCT Pub. Date: Apr. 12, 2012

(65) Prior Publication Data
US 2013/0224162 A1 Aug. 29, 2013

(30) Foreign Application Priority Data
Oct. 8, 2010 (KR) .......................... 10-2010-0098234

(51) Int. Cl.
*A61K 35/30* (2015.01)
*C12N 5/0797* (2010.01)
*C12N 9/10* (2006.01)
*A61K 48/00* (2006.01)

(52) U.S. Cl.
CPC ............... *A61K 35/30* (2013.01); *A61K 48/005* (2013.01); *C12N 5/0623* (2013.01); *C12N 9/1029* (2013.01); *C12Y 203/01006* (2013.01); *C12N 2510/00* (2013.01)

(58) Field of Classification Search
CPC ..................................................... A61K 38/43
See application file for complete search history.

(56) References Cited

U.S. PATENT DOCUMENTS

| | | | |
|---|---|---|---|
| 6,656,743 B2 * | 12/2003 | Huson et al. ................... | 435/193 |
| 2004/0138117 A1 * | 7/2004 | Hudson et al. .................. | 514/12 |
| 2007/0054278 A1 * | 3/2007 | Cargill ............................. | 435/6 |

FOREIGN PATENT DOCUMENTS

| WO | WO 2006/102902 | 10/2006 | ............... C12N 5/00 |
|---|---|---|---|
| WO | WO 2006102902 A1 * | 10/2006 | |

OTHER PUBLICATIONS

Xuan et al. "Effects of engrafted neural stem cells in Alzheimer's disease rats." Neurosci Lett. Jan. 30, 2009;450(2):167-71.*

Kim et al. "Brain transplantation of human neural stem cells transduced with tyrosine hydroxylase and GTP cyclohydrolase 1 provides functional improvement in animal models of Parkinson disease." Neuropathology. Apr. 2006;26(2):129-40.*

Lee et al. "Human neural stem cells over-expressing VEGF provide neuroprotection, angiogenesis and functional recovery in mouse stroke model." PLoS One. Jan. 17, 2007;2(1):e156.*

Zhong et al., "Discrete Acetylcholine Release from Neuroblastoma or Hybrid Cells Overexpressing Choline Acetyltransferase into the Neuromuscular Synaptic Cleft," *Neuroscience Research* 22: 81-88, 1995.

Zhong et al., "Overexpression of Choline Acetyltransferase Reconstitutes Discrete Acetylcholine Release in Some but Not All Synapse Formation-Defective Neuroblastoma Cells," *J. Physiology* 89: 137-145, 1995.

International Search Report for PCT/KR2011/004886, mailed Feb. 10, 2012 (4 pages).

Kim, Seung U., *"Human neural stem cells genetically modified for brain repair in neurological disorders"*, Neuropathology 2004; 24, 159-171.

Lee, Hong J., et al., *"Human Neural Stem Cells Genetically Modified to Express Human Nerve Growth Factor (NGF) Gene Restore Cognition in the Mouse With Ibotenic Acid-Induced Cognitive Dysfunction"*, Cell Transplantation, vol. 21, pp. 2487-2496, 2012, 10 pages.

Park, Dongsun, et al., *"Human Neural Stem Cells Overexpressing Choline Acetyltransferase Restore Cognitive Function of Kainic Acid-Induced Learning and Memory Deficit Animals"*, Cell Transplantation, vol. 21, pp. 365-371, 2012.

Park, Dongsun, et al., *"Human neural stem cells over-expressing choline acetyltransferase restore cognition in rat model of cognitive dysfunction"*, Experimental Neurology 234 (2012) 521-526.

Park, Dongsun, et al., *"Improvement of cognitive function and physical activity of aging mice by human neural stem cells over-expressing choline acetyltransferase"*, Neurobiology of Aging 34 (2013) 2639-2646.

(Continued)

*Primary Examiner* — Thaian N Ton
*Assistant Examiner* — Titilayo Moloye
(74) *Attorney, Agent, or Firm* — Harness, Dickey & Pierce, P.L.C.

(57) ABSTRACT

The present invention relates to human neural stem cells (NSCs) transfected with a vector comprising a polynucleotide encoding human choline acetyltransferase (ChAT) and thereby stably expressing the human ChAT, a composition for treating Alzheimer disease or for improving a cognitive disorder comprising the human NSCs expressing a human ChAT. The present human NSCs genetically modified to express human ChAT, when transplanted into the brain of the animal AD model, successfully integrated into the host tissues and differentiated into the normal neuronal cells or glial cells. The instant genetically modified human NSCs stably express ChAT in the brain tissue of AD animal and thereby restore the acetylcholine level, and learning and memory function comparable to normal animal. The present genetically modified human NSCs expressing ChAT can be used for the treatment of AD as well as cognitive disorders due to other brain diseases and aging.

6 Claims, 4 Drawing Sheets

(56) References Cited

OTHER PUBLICATIONS

Yasuhara, Takao; "Transplantation of Human Neural Stem Cells Exerts Neuroprotection in a Rat Model of Parkinson's Disease", The Journal of Neuroscience, Nov. 29, 2006; 26(48):12497-12511.

Lee, Hong J., et al., "Brain Transplantation of Immortalized Human Neural Stem Cells Promotes Functional Recovery in Mouse Intracerebral Hemorrhage Stroke Model"; Stem Cells 2007;25:1204-1212.

Long, A.G. Xuan, et al., "BDNF improves the effects of neural stem cells on the rat model of Alzheimer's disease with unilateral lesion of fimbriafornix", Neuroscience Letters 440 (2008) 331-335.

Blurton-Jones, Mathew, et al., "Neural stem cells improve cognition via BDNF in a transgenic model of Alzheimer disease", PNAS, Aug. 11, 2009, vol. 106 No. 32, 6 pages.

Hwang, Dong H., et al., "Transplantation of human neural stem cells transduced with Olig2 transcription factor improves locomotor recovery and enhances myelination in the white matter of rat spinal cord following contusive injury", BMC Neuroscience 2009, 10:117 doi:10.1186/1471-2202-10-117, 16 pages.

* cited by examiner

SEQUENCE LISTING

```
<160> NUMBER OF SEQ ID NOS: 3

<210> SEQ ID NO 1
<211> LENGTH: 748
<212> TYPE: PRT
<213> ORGANISM: Homo sapiens

<400> SEQUENCE: 1

Met Gly Leu Arg Thr Ala Lys Lys Arg Gly Leu Gly Gly Gly Gly Lys
1               5                   10                  15

Trp Lys Arg Glu Glu Gly Gly Gly Thr Arg Gly Arg Arg Glu Val Arg
            20                  25                  30

Pro Ala Cys Phe Leu Gln Ser Gly Gly Arg Gly Asp Pro Gly Asp Val
        35                  40                  45

Gly Gly Pro Ala Gly Asn Pro Gly Cys Ser Pro His Pro Arg Ala Ala
    50                  55                  60

Thr Arg Pro Pro Pro Leu Pro Ala His Thr Pro Ala His Thr Pro Glu
65                  70                  75                  80

Trp Cys Gly Ala Ala Ser Ala Glu Ala Ala Glu Pro Arg Arg Ala Gly
                85                  90                  95

Pro His Leu Cys Ile Pro Ala Pro Gly Leu Thr Lys Thr Pro Ile Leu
            100                 105                 110
```

-continued

```
Glu Lys Val Pro Arg Lys Met Ala Ala Lys Thr Pro Ser Glu Glu
            115                 120                 125

Ser Gly Leu Pro Lys Leu Pro Val Pro Pro Leu Gln Gln Thr Leu Ala
        130                 135                 140

Thr Tyr Leu Gln Cys Met Arg His Leu Val Ser Glu Glu Gln Phe Arg
145                 150                 155                 160

Lys Ser Gln Ala Ile Val Gln Phe Gly Ala Pro Gly Gly Leu Gly
                165                 170                 175

Glu Thr Leu Gln Gln Lys Leu Leu Glu Arg Gln Lys Thr Ala Asn
                180                 185                 190

Trp Val Ser Glu Tyr Trp Leu Asn Asp Met Tyr Leu Asn Asn Arg Leu
        195                 200                 205

Ala Leu Pro Val Asn Ser Ser Pro Ala Val Ile Phe Ala Arg Gln His
        210                 215                 220

Phe Pro Gly Thr Asp Asp Gln Leu Arg Phe Ala Ala Ser Leu Ile Ser
225                 230                 235                 240

Gly Val Leu Ser Tyr Lys Ala Leu Leu Asp Ser His Ser Ile Pro Thr
                245                 250                 255

Asp Cys Ala Lys Gly Gln Leu Ser Gly Gln Pro Leu Cys Met Lys Gln
                260                 265                 270

Tyr Tyr Gly Leu Phe Ser Ser Tyr Arg Leu Pro Gly His Thr Gln Asp
        275                 280                 285

Thr Leu Val Ala Gln Asn Ser Ser Ile Met Pro Glu Pro Glu His Val
        290                 295                 300

Ile Val Ala Cys Cys Asn Gln Phe Phe Val Leu Asp Val Val Ile Asn
305                 310                 315                 320

Phe Arg Arg Leu Ser Glu Gly Asp Leu Phe Thr Gln Leu Arg Lys Ile
                325                 330                 335

Val Lys Met Ala Ser Asn Glu Asp Glu Arg Leu Pro Pro Ile Gly Leu
                340                 345                 350

Leu Thr Ser Asp Gly Arg Ser Glu Trp Ala Glu Ala Arg Thr Val Leu
        355                 360                 365

Val Lys Asp Ser Thr Asn Arg Asp Ser Leu Asp Met Ile Glu Arg Cys
370                 375                 380

Ile Cys Leu Val Cys Leu Asp Ala Pro Gly Gly Val Glu Leu Ser Asp
385                 390                 395                 400

Thr His Arg Ala Leu Gln Leu Leu His Gly Gly Tyr Ser Lys Asn
                405                 410                 415

Gly Ala Asn Arg Trp Tyr Asp Lys Ser Leu Gln Phe Val Val Gly Arg
        420                 425                 430

Asp Gly Thr Cys Gly Val Val Cys Glu His Ser Pro Phe Asp Gly Ile
        435                 440                 445

Val Leu Val Gln Cys Thr Glu His Leu Leu Lys His Met Thr Gln Ser
450                 455                 460

Ser Arg Lys Leu Ile Arg Ala Asp Ser Val Ser Glu Leu Pro Ala Pro
465                 470                 475                 480

Arg Arg Leu Arg Trp Lys Cys Ser Pro Glu Ile Gln Gly His Leu Ala
                485                 490                 495

Ser Ser Ala Glu Lys Leu Gln Arg Ile Val Lys Asn Leu Asp Phe Ile
                500                 505                 510

Val Tyr Lys Phe Asp Asn Tyr Gly Lys Thr Phe Ile Lys Lys Gln Lys
        515                 520                 525

Cys Ser Pro Asp Ala Phe Ile Gln Val Ala Leu Gln Leu Ala Phe Tyr
```

```
                530                 535                 540
Arg Leu His Arg Arg Leu Val Pro Thr Tyr Glu Ser Ala Ser Ile Arg
545                 550                 555                 560

Arg Phe Gln Glu Gly Arg Val Asp Asn Ile Arg Ser Ala Thr Pro Glu
                565                 570                 575

Ala Leu Ala Phe Val Arg Ala Val Thr Asp His Lys Ala Ala Val Pro
                580                 585                 590

Ala Ser Glu Lys Leu Leu Leu Lys Asp Ala Ile Arg Ala Gln Thr
            595                 600                 605

Ala Tyr Thr Val Met Ala Ile Thr Gly Met Ala Ile Asp Asn His Leu
            610                 615                 620

Leu Ala Leu Arg Glu Leu Ala Arg Ala Met Cys Lys Glu Leu Pro Glu
625                 630                 635                 640

Met Phe Met Asp Glu Thr Tyr Leu Met Ser Asn Arg Phe Val Leu Ser
                645                 650                 655

Thr Ser Gln Val Pro Thr Thr Thr Glu Met Phe Cys Cys Tyr Gly Pro
                660                 665                 670

Val Val Pro Asn Gly Tyr Gly Ala Cys Tyr Asn Pro Gln Pro Glu Thr
            675                 680                 685

Ile Leu Phe Cys Ile Ser Ser Phe His Ser Cys Lys Glu Thr Ser Ser
            690                 695                 700

Ser Lys Phe Ala Lys Ala Val Glu Glu Ser Leu Ile Asp Met Arg Asp
705                 710                 715                 720

Leu Cys Ser Leu Leu Pro Pro Thr Glu Ser Lys Pro Leu Ala Thr Lys
                725                 730                 735

Glu Lys Ala Thr Arg Pro Ser Gln Gly His Gln Pro
            740                 745

<210> SEQ ID NO 2
<211> LENGTH: 19
<212> TYPE: DNA
<213> ORGANISM: Homo sapiens

<400> SEQUENCE: 2
ctgtgccccc ttctagagc                                                19

<210> SEQ ID NO 3
<211> LENGTH: 18
<212> TYPE: DNA
<213> ORGANISM: Homo sapiens

<400> SEQUENCE: 3
caaggttggt gtccctgg                                                 18
```

HUMAN NEURAL STEM CELLS EXPRESSING HUMAN CHOLINE ACETYLTRANSFERASE, AND USE THEREOF

CROSS-REFERENCE TO RELATED APPLICATIONS

This application is the U.S. national stage filing under 35 U.S.C. §371 of International Application No. PCT/KR2011/004886, filed Jul. 4, 2011, which claims priority from Korean Patent Application No. 10-2010-0098234, filed on Oct. 08, 2010, in the Korean Intellectual Property Office, the disclosure of which is incorporated herein by reference.

FIELD OF THE INVENTION

The present invention relates to human neural stem cells (NSCs) transfected with a vector comprising a polynucleotide encoding human choline acetyltransferase (ChAT) and thereby stably expressing the human ChAT. More specifically, the present invention relates to a pharmaceutical composition for treating Alzheimer disease or for improving a cognitive disorder comprising human NSCs expressing a human ChAT.

DESCRIPTION OF THE RELATED ART

Alzheimer disease (AD) is one of the most devastating neurodegenerative diseases, which is characterized by deficit of cognitive functions including learning and memory loss (1). In AD patients, the dysfunction of presynaptic cholinergic system is one of the primary causes of cognitive disorders (2, 3), in which decreased activity of enzyme choline acetyltransferase (ChAT) responsible for acetylcholine (Ach) synthesis is observed (4, 5). To date, AD therapy is largely based on small molecule designed to increase ACh concentration by inhibiting acetylcholinesterase (AChE), an AChdegrading enzyme (5, 6). Since therapy with the drugs is only palliative without potential protection against progressive tissue destruction, there is substantial need for effective therapies for patients with AD, and stem cell-based therapeutic approach targeting AD should fulfill this requirement.

For many neurological disorders, studies have begun to examine stem cell-based therapies as a novel strategy to treat disorders such as Parkinson disease (PD), Huntington disease, amyotrophic lateral sclerosis (ALS), stroke and spinal cord injury (7-9). In contrast to a transient improvement of body function by pharmaceuticals, it is expected that stem cells can prevent or delay host cell death and restore injured tissue (7-10). Notably, we have previously demonstrated that transplantation of human neural stem cells (NSCs) expressing diverse functional genes, especially encoding growth factors, preserves host cells and recovered body function in animal models of stroke, PD, ALS, and spinal cord injury (11-14). Immortalized human NSCs have emerged as highly-effective source of cells for genetic manipulation and gene transfer into the central nervous system (CNS) ex vivo; genetically modified NSCs survive, integrate into host tissues and differentiate into both neurons and glial cells after transplantation into intact or damaged brain (9).

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THIS INVENTION

Technical Purposes of This Invention

The present inventors have made intensive studies to develop a stem cell-based therapeutics for alleviating cognitive disorders such as learning or memory dysfunction in Alzheimer disease patients who lack acetylcholine. The instant inventors established human neuronal stem cell (NSC) lines over-expressing human choline acetyltransferase (ChAT) and transplanted the prepared human NSCs into the brain of animal of Alzheimer disease model. As a result, the inventors demonstrated that the transplanted human NSCs over-expressing human ChAT stably differentiates into normal neuron cells in the brain of the animal and successfully recover the learning and memory function of the Alzheimer disease animal.

Accordingly, it is an object of this invention to provide human neural stem cells (NSCs) expressing human choline acetyltransferase (ChAT).

It is another object of this invention to provide a pharmaceutical composition for treating Alzheimer disease comprising human NSCs expressing human ChAT.

It is still another object of this invention to provide a pharmaceutical composition for improving a cognitive disorder comprising human NSCs expressing human ChAT.

It is still another object of this invention to provide a method of treating Alzheimer disease comprising administering to a subject suffering from Alzheimer disease a pharmaceutically effective amount of human NSCs expressing human ChAT.

It is still another object of this invention to provide a method of improving a cognitive disorder comprising administering to a subject suffering from cognitive disorder a pharmaceutically effective amount of human NSCs expressing human ChAT.

It is still another object of this invention to provide a pharmaceutical composition comprising human NSCs expressing human ChAT for use in a method of treating Alzheimer disease.

It is still another object of this invention to provide a pharmaceutical composition comprising human NSCs expressing human ChAT for use in a method of treating a cognitive disorder.

Other objects and advantages of the present invention will become apparent from the following detailed description together with the appended claims and drawings.

DETAILED DESCRIPTION OF THIS INVENTION

In one aspect of this invention, there is provided human neural stem cells (NSCs) transfected with a vector comprising a polynucleotide encoding human choline acetyltransferase (ChAT) and thereby stably expressing human choline acetyltransferase.

The term "choline acetyltransferase (ChAT)" used herein refers to an enzyme responsible for the synthesis of neurotransmitter acetylcholine by combining acetyl-CoA with choline. The acetylcholine is produced in the body of neuron and moved into the terminal of the neuron through the axoplasmic flow. The choline acetyltransferase is encoded by the ChAT gene in human [Strauss, W. L., Kemper R. R., Jayakar, P. et al., Genomics 9, 396-398 (1991)].

According to a preferred embodiment, the choline acetyltransferase comprises the amino acid sequence of SEQ ID NO:1 (GenBank Accession No. NP_065574).

The term "neural stem cells (NSCs)" used herein refers to cells that can continuously self-renew and have the multipotential to generate neurons (neuronal cells), astrocytes, and oligodendrocytes constituting the central nervous system.

According to a preferred embodiment, the neural stem cells of this invention are primary cultured neural stem cells or genetically modified immortalized neural stem cells.

The human neural stem cells of the present invention can be primary cultured neural stem cells isolated from various tissue of the human. For example, neural stem cells isolated from a human adult brain or fetal brain, neural stem cells induced from hematopoietic stem cells in a human cord blood or bone marrow, or neural stem cells derived from a human embryo can be used for the present invention.

The human neural stem cells of the present invention can be genetically modified immortalized one. For example, immortalized neural stem cells established by introducing a retroviral vector containing v-myc oncogene can be used for the present invention.

Human neural stem cells can be identified by positive staining of the stem cell marker of Nestin.

The detailed method for preparing neural stem cells is described in U.S. Pat. No. 5,654,183 and is incorporated herein as a reference. Human neural stem cells can be cultured in the media in the presence of growth factors such as bFGF (basic fibroblast growth factor), EGF (epidermal growth factor), or FGF (fibroblast growth factor) with a suitable concentration, for example 5-100 ng/ml.

The human neural stem cells of the present invention are genetically modified cells which have been transfected with a vector comprising human choline acetyltransferase (ChAT).

As demonstrated by the following specific examples of the present invention, human choline acetyltransferase (ChAT), which is introduced into the human neural stem cells (NSCs) through the viral vector, is stably expressed in the host cells. Furthermore, the present human NCSs expressing the human ChAT, when transplanted into the brain of animal of Alzheimer disease model, stably survive, integrate into the host brain tissues, and differentiate into neurons and astrocytes, and eventually restore cognitive functions comparable to the normal animal by elevating the acetylcholine level.

The vector that can be used for the introduction of human ChAT gene into the human NSCs in the present invention preferably includes without limitation (i) adenoviral vector, (ii) retroviral vector, (iii) adeno-associated viral vector, (iv) herpes simplex viral vector, (v) SV 40 vector, (vi) polyoma viral vector, (vii) papilloma viral vector, (viii) picornaviral vector, (ix) vaccinia viral vector, and (x) helper-dependent adenoviral vector.

The replication origin that can be used in the present vector is preferably operable in the eukaryotic cells, and more preferably comprises without limitation f1 replication origin, SV40 replication origin, pMB1 replication origin, Adeno replication origin, AAV replication origin, and BBV replication origin.

The promoter that can be used in the present vector preferably includes without limitation the promoters derived from the genome of mammalian cells (e.g. metallothionein promoter) or derived from mammalian viruses (e.g. the adenovirus late promoter, the vaccinia virus 7.5K promoter, SV40 promoter, cytomegalovirus promoter, and HSV tk promoter). The polyadenylation sequence as a transcription termination signal sequence that can be used in the instant vector preferably includes without limitation SV40-derived polyadenylation sequence or BGH polyA sequence.

According to this invention, the vector may include a suitable selective marker, preferably includes antibiotic resistance gene, such as the resistance genes for ampicillin, gentamicin, carbenicillin, chloramphenicol, streptomycin, kanamycin, geneticin, neomycin, puromycin, or tetracycline.

Figure 1:
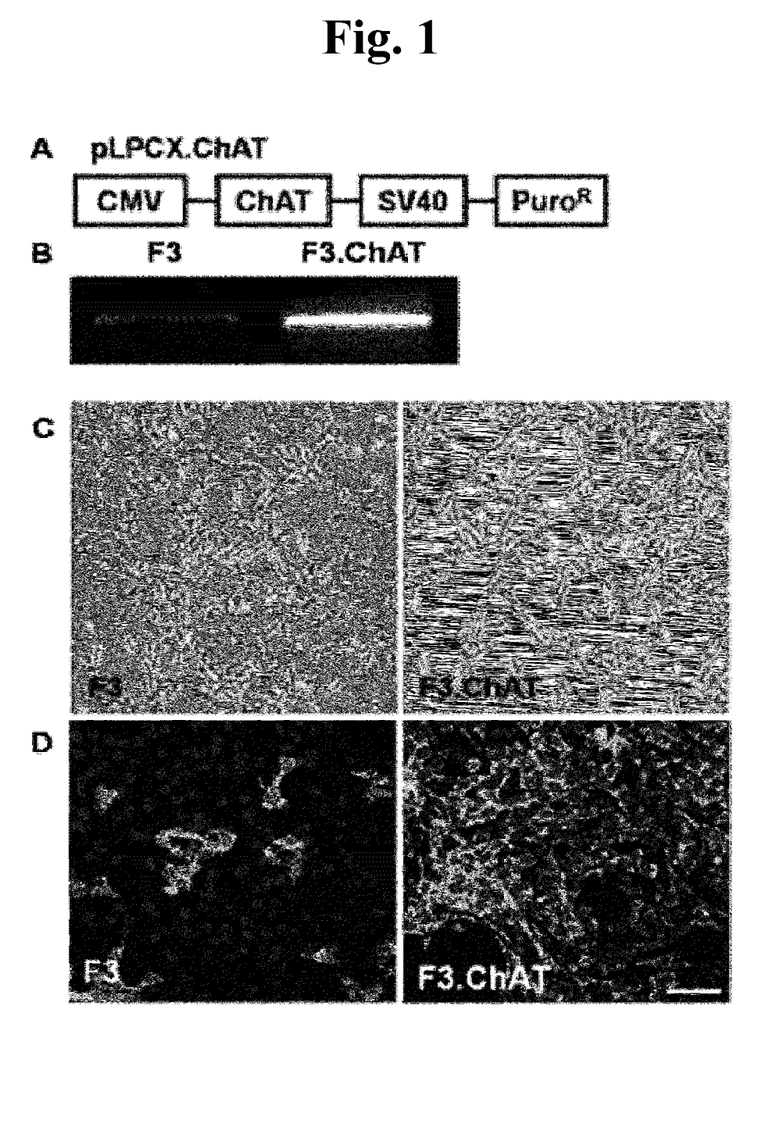
FIG. 1 represents F3.ChAT human neural stem cell line generated by infecting F3 human neural stem cells with retroviral vector encoding human ChAT gene. Panel (A) depicts the structure of the retroviral vector. The plasmid, pLPCX-.ChAT contains the full-length human ChAT cDNA. Panel (B) shows the results of RT-PCR analysis of ChAT mRNA expression. Panel (C) displays the morphology of F3 (left) and F3.ChAT (right) cells. Panel (D) shows ChAT protein (green-colored) in F3 (left) and F3.ChAT (right) cells detected by the immunocytochemical method. Scale bar, 50 µm. An immortalized NSC line, HB1.F3 (F3), was established from primary cultures of a 15-week gestational human fetal brain by infecting with a retroviral vector encoding v-myc oncogene (9, 11, 28). The F3 NSC line was infected with a retrovirus encoding human ChAT gene. Plasmid pLPCX.ChAT containing the full-length human ChAT cDNA was used. PG13 mouse packaging cell line was transfected with pLPCX.ChAT vector using SuperFect reagent, and stable PG13 cell line were selected using 5 μg/ml puromycin for 7 days. Replication incompetent retroviral vector collected from PG13.ChAT cells was used for infection of F3 human NSCs and puromycin-resistant F3.ChAT clones were isolated, and one of the clones F3.ChAT.D2 was expanded, and used for the transplantation. For analysis of ChAT mRNA expression, RT-PCR was performed. For demonstration of ChAT protein, cells were incubated with primary antibody specific for human ChAT followed by fluorescent 2nd antibody, and viewed under a laser-scanning confocal microscope.

According to the most preferred embodiment of this invention, the structure of the vector for expressing a human choline acetyltransferase is depicted in the panel A of FIG. 1.

The introduction of the vector into human neural stem cells can be performed through various methods known to those skilled in the art, for example, microinjection [Capecchi, M. R., Cell, 22:479 (1980)], calcium phosphate co-precipitation [Graham, F. L. et al., Virology, 52:456 (1973)], electroporation [Neumann, E. et al., EMBO J., 1:841 (1982)], liposome-mediated transfection [Wong, T. K. et al., Gene, 10:87 (1980)], DEAE-dextran treatment [Gopal, Mol. Cell Biol., 5:1188-1190 (1985)], and particle bombardment [Yang et al., Proc. Natl. Acad. Sci., 87:9568-9572 (1990)].

The human neural stem cells that are transfected with the vector containing ChAT gene can be easily selected by utilizing the phenotype expressed by selection marker. For example, if the selection marker is the resistance gene for the particular antibiotic, the transformed human NSCs can be selected by cultivating the host cells in the media containing the antibiotic.

In another aspect of this invention, there is provided a pharmaceutical composition for treating Alzheimer disease comprising human neural stem cells transfected with a vector comprising a polynucleotide encoding human choline acetyltransferase and thereby stably expressing human choline acetyltransferase.

The pharmaceutical composition according to this invention may typically be prepared as injectables, either as liquid solutions or suspensions containing the cells. Pharmaceutical forms suitable for injection include sterile aqueous solutions or dispersions for extemporaneous preparation of the solutions or dispersions. In all cases the form must be sterile and must be fluid to the extent that is feasible for injection.

The pharmaceutical composition may include pharmaceutically acceptable carrier compatible with human neural stem cells. The term "pharmaceutically acceptable" refers to molecular entities and compositions that do not produce an allergic or similar untoward reaction when administered to a human. The pharmaceutically acceptable carrier includes any solvents, dispersion media, coatings, antibacterial and antifungal agents, isotonic and absorption delaying agents and the like. The use of such media and agents for pharmaceutically active substances is well known in the art. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained by the use of a coating such as lecithin. The prevention of the contamination of microorganisms can be accomplished by the use of various antibacterial and antifungal agents such as parabens, chlorobutanol, phenol, sorbic acid, thimerosal and the like. In many cases, isotonic agents may be included, for example, sugars or sodium chloride. Prolonged adsorption of the injectable compositions can be brought about by the use in the composition of agents delaying absorption, for example, aluminum monostearate and gelatin. Sterile injectable solutions are prepared by incorporating the active agents in the required amount in the appropriate solvent with various other ingredients followed by filtered sterilization.

The pharmaceutical composition according to this invention is preferably administered parenterally, i.e., by intraperitoneal, subcutaneous, intramuscular, intravenous, intracerebroventricular, intraspinal or local administration. Most preferably, the pharmaceutical composition of this invention can be administered by direct injection into the brain region.

The pharmaceutical composition according to this invention may be administered in a manner compatible with the dosage formulation and in such amount as is therapeutically effective. A suitable dosage amount of the pharmaceutical composition of this invention may vary depending on the condition of the subject being treated. For parenteral administration in an aqueous solution, for example, the solution should be suitably buffered if necessary and the liquid diluents first rendered isotonic with sufficient saline or glucose. These particular aqueous solutions are especially suitable for intravenous, intramuscular, subcutaneous, intradermal, intracerebroventricular, intraspinal and intraperitoneal administration. In this connection, carrier, formulation, and media that can be employed in the present composition are well known to those skilled in the art. See for example, "Remington's Pharmaceutical Sciences" $15^{th}$ Edition.

In still another aspect of this invention, there is provided a composition for improving a cognitive disorder comprising human neural stem cells (NSCs) transfected with a vector comprising a polynucleotide encoding human choline acetyltransferase (ChAT) and thereby stably expressing human ChAT.

According to a preferred embodiment, the cognitive disorder is a disorder of learning function or memory function.

According to another preferred embodiment, the cognitive disorder is caused by the reduction of level of acetylcholine released in the brain.

According to still another preferred embodiment, the composition for improving a cognitive disorder is formulated as a form of pharmaceutical composition. Since the pharmaceutical composition for treating Alzheimer disease is described herein above and therefore the above descriptions can be adapted to the pharmaceutical composition for improving a cognitive disorder. Accordingly, the common descriptions between them are omitted in order to avoid undue redundancy leading to the complexity of this specification.

In still another aspect of this invention, there is provided a method of treating Alzheimer disease comprising administering to a subject suffering from Alzheimer disease a pharmaceutically effective amount of human neural stem cells (NSCs) transfected with a vector comprising a polynucleotide encoding human choline acetyltransferase (ChAT) and thereby stably expressing human ChAT.

In still another aspect of this invention, there is provided a method of treating a cognitive disorder comprising administering to a subject suffering from a cognitive disorder a pharmaceutically effective amount of human neural stem cells (NSCs) transfected with a vector comprising a polynucleotide encoding human choline acetyltransferase (ChAT) and thereby stably expressing human ChAT.

In still another aspect of this invention, there is provided a pharmaceutical composition comprising a human neural stem cells (NSCs) transfected with a vector comprising a polynucleotide encoding human choline acetyltransferase (ChAT) and thereby stably expressing human ChAT for use in a method of treating Alzheimer disease.

In still another aspect of this invention, there is provided a use of a human neural stem cells (NSCs) transfected with a vector comprising a polynucleotide encoding human choline acetyltransferase (ChAT) and thereby stably expressing human ChAT for the manufacture of a medicament for use in treatment of Alzheimer disease.

In still another aspect of this invention, there is provided a pharmaceutical composition comprising a human neural stem cells (NSCs) transfected with a vector comprising a polynucleotide encoding human choline acetyltransferase (ChAT) and thereby stably expressing human ChAT for use in a method of treating a cognitive disorder.

In still another aspect of this invention, there is provided a use of a human neural stem cells (NSCs) transfected with a vector comprising a polynucleotide encoding human choline acetyltransferase (ChAT) and thereby stably expressing human ChAT for the manufacture of a medicament for use in treatment of a cognitive disorder.

Advantageous Effects

The present invention relates to human neural stem cells (NSCs) transfected with a vector comprising a polynucleotide encoding human choline acetyltransferase (ChAT) and thereby stably expressing the human ChAT. More specifically, the present invention relates to a pharmaceutical composition for treating Alzheimer disease or for improving a cognitive disorder comprising the human NSCs expressing a human ChAT. The features and advantages of the present invention will be summarized as follows:

(i) the present human NSCs genetically modified to express human ChAT, when transplanted into the brain of the animal AD model, successfully integrated into the host tissues and differentiated into the normal neuronal cells or glial cells.

(ii) the present genetically modified human NSCs stably express ChAT in the brain tissue transplanted and thereby restore the acetylcholine level comparable to the normal level.

(iii) the present genetically modified human NSCs expressing ChAT restore the cognitive functions including learning and memory functions in the animal AD model.

(iv) the present genetically modified human NSCs expressing ChAT can be used for the treatment of Alzheimer disease as well as cognitive disorders due to other brain diseases and aging.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Human Choline Acetyltransferase (ChAT) Cloning and cDNA Constructs

Full length cDNA of human choline acetyltransferase (ChAT) was obtained by PCR from human small intestine Marathon-Ready cDNA (Clontech, Mountain View, Calif.) following the procedures previously described for rat peripheral type ChAT (29). Sequencing of plasmid DNA was determined with ABI 3100 DNA sequencer (Applied Biosystems, Foster City, Calif.).

Example 2

Human Neural Stem Cell (NSC) Lines

HB1.F3 (F3) human NSC line (8, 9, 11, 28) was infected with a retrovirus with pLPCX.ChAT containing the full-length human ChAT cDNA, selected for puromycin resistance (13). F3.ChAT, ChAT-overexpressing clone, was isolated, and expression of ChAT was analyzed by RT-PCR and immunofluorescence microscopy.

Example 3

RT-PCR Analysis

Total RNA was extracted from NSC cultures using TRIzol (BRL, Gaithersburg, Md.). Complimentary DNA templates were prepared from 1 mg of total RNA primed with oligo dT primers using 400 U of Moloney Murine Leukemia Virus reverse transcriptase (Promega, Madison, Wis.) followed by 25 PCR cycles, and RT-PCR products were separated electrophoretically on 1.2% agarose gel containing ethidium bromide. The primers used for the ChAT RT-PCR are following:

```
                                        (SEQ ID NO: 2)
    Sense:      5'-CTGTGCCCCCTTCTAGAGC-3';

(SEQ ID NO: 3)
    Antisense:  5'-CAAGGTTGGTGTCCCTGG-3'.
```

Example 4

Immunocytochemistry of NSCs

F3.ChAT cells were plated on poly-L-lysine-coated Aclar plastic coverslips and fixed in 4% paraformaldehyde in 0.1 M phosphate buffer for 5 min at room temperature. Fixed cultures were incubated with the primary antibody specific for human ChAT (1:100, rabbit polyclonal, Chemicon, Temecula, Calif.) for 24 hr at 4° C., followed by Alexa Fluor 488-conjugated anti-rabbit IgG (Molecular Probes, Eugene, OR) for 1 hr at room temperature (RT). Cells were counterstained with 4',6-diamino-2-phenylindole (DAPI, Sigma, St. Louis, Mo.) to identify cellular nuclei.

Example 5

AD Model and NSCs Transplantation

Male Sprague-Dawley rats (Orient-Bio, Seongnam, Korea) weighing between 220-230 g were anesthetized with enflurane and positioned in a stereotaxic frame. After incision of the skin and drilling a hole, freshly-prepared AF64A (RBI, Natick, Mass.) solution (3 nmol/3 µl/rat) (17, 20) was infused into the right ventricle, at the following stereotaxic coordinates from bregma: posterior 0.8 mm, lateral 1.5 mm, and ventral 4.0 mm, at a flow rate of 0.5 µl/min (17, 21). Two weeks later, F3 or F3·ChAT cells ($1 \times 10^6$ cells/rat) were transplanted in rats showing loss of learning and memory functions (n=15/group) via intracerebroventricular (icy) injection at the same coordinates.

Example 6

Learning/Memory Testing

The rats were subjected to learning and memory function tests 4-5 weeks (n=8/group) or 8-9 weeks (n=7/group) after transplantation of the cells. The passive avoidance trials were performed once a day for consecutive 4 days and 5th trial 1 week after the 4th trial for the evaluation of memory acquisition and retention. The latency time of stay in the light room from light-on was recorded following experience of electric shock (1 mA for 2 sec) in the dark compartment. Water-maze trials were performed in a circular water bath filled with water maintained at 22±2° C. The bath was divided into 4 quadrants and a hidden escape platform (10 cm in diameter) was submerged in the center of one quadrant. The rats were trained to learn to find the hidden platform, based on several cues external to the maze. Three trials were conducted on each day with 5-min intervals for the 4 consecutive days followed by 5th performance 1 week after the 4th day trial. The mean time spent to escape onto the platform was recorded.

Example 7

Acetylcholine Analysis in CSF

The rats were sacrificed at the end of learning/memory testing, and cerebrospinal fluid (CSF) was collected to analyze acetylcholine (ACh) contents. ACh concentration in CSF was measured with the Amplex Red acetylcholine/acetylcholinesterase assay kit (Molecular Probes) according to the manufacturer's instructions.

Example 8

Immunohistochemistry in Brain Sections

The rat brains were perfusion-fixed with 4% paraformaldehyde solution and post-fixed for 48 hr, followed by cryoprotection in 30% sucrose for 72 hr. Coronal cryosections 30-μm thick were prepared and processed for double immunostaining of human nuclear matrix antigen (hNuMA) and ChAT, neurofilament protein (for neurons) or GFAP (for astrocytes) using antibodies specific for hNuMA (1:100, mouse monoclonal, EMD Biosciences, San Diego, Calif.), ChAT (1:100, rabbit polyclonal, Chemicon), NF-Mix (1:1, 000, rabbit polyclonal, Chemicon) or GFAP (1:1,000, rabbit polyclonal, Chemicon). Brain sections were incubated with primary antibodies overnight at 4° C. and with secondary antibodies conjugated with Alexa Fluor-488 or -594 (1:1,000, Molecular Probes) for 1 hr at RT.

Example 9

Statistical Analysis

Data are presented as means±sem. The statistical significance between group comparisons for behavioral data was determined by one-way analysis of variance (ANOVA) and two-way ANOVA. P-values<0.05 were considered to be statistically significant.

Example 10

Establishment of Human NSC Lines Expressing ChAT

Transfection of F3 human NSCs with human ChAT gene (FIG. 1A) was confirmed by reverse transcriptase-polymerase chain reaction (RT-PCR) analysis, displaying expression of ChAT mRNA in F3.ChAT cells (FIG. 1B). The expression levels of ChAT mRNA and protein in F3.ChAT cells are significantly higher than those in F3 cells (FIGS. 1B and 1D). The F3.ChAT cells showed similar morphology to their parental F3 cells (FIG. 1C) and F3.ChAT cells were highly immunoreaction-positive for ChAT antibody (FIG. 1D).

Example 11

Transplantation of F3.ChAT Cells into the Rat Brain Pre-treated with AF64A

At 9 weeks after icy transplantation of F3.ChAT cells ($1 \times 10^6$ cells/rat) in AF64A-challenged rats, it was confirmed that F3.ChAT cells were distributed diffusely all over the brain regions (FIGS. 2A to 2D). ChAT-immnuoreactivity was detected in hippocampus, thalamus, hypothalamus, cortices and septum. In order to confirm transplanted F3.ChAT cells express ChAT activity in vivo, the inventors performed double immunostaining using antibodies specific for human nuclear matrix antigen (hNuMA) and ChAT, and the results indicate that most of the huNuMA-positive F3.ChAT cells strongly express ChAT at 9 weeks post-transplantation (FIG. 2E). In addition, F3.ChAT cells double-positive for hNuMA and glial fibrillary acidic protein (GFAP) as well as double-positive for hNuMA and neurofilament (NF) were found indicating that F3.ChAT cells differentiate into both astrocytes and neurons (FIGS. 2F and 2G). The ChAT protein was detected in the F3.ChAT cells which were diffused and distributed all over the brain regions of rat AD model after transplantation. The injected F3.ChAT cells survived in vivo up to 9 weeks after transplantation (FIG. 2).

Example 12

Restoration of the Acetylcholine Concentration by the Transplantation of F3.ChAT Cells AF64A is a choline analogue which is taken up only by the high-affinity choline transport system into cholinergic neurons, and causes alterations in ChAT mRNA expression and enzyme activity (15-17). Hence, AF64A administration was found to decrease the release of ACh, and thereby induce cognitive impairments including memory and learning deficits (16-18). Therefore, the inventors adopted AF64A animal model to match the concept of memory improvement by F3.ChAT transplantation. Only decrease by 25-30% of ACh levels leads to a severe memory loss not only in β-amyloid transgenic (Tg2576) mice (19), but also in AF64A-injected animals who revealed symptoms within 2 weeks, lasting longer than 11 weeks (16-18, 20).

Figure 3:
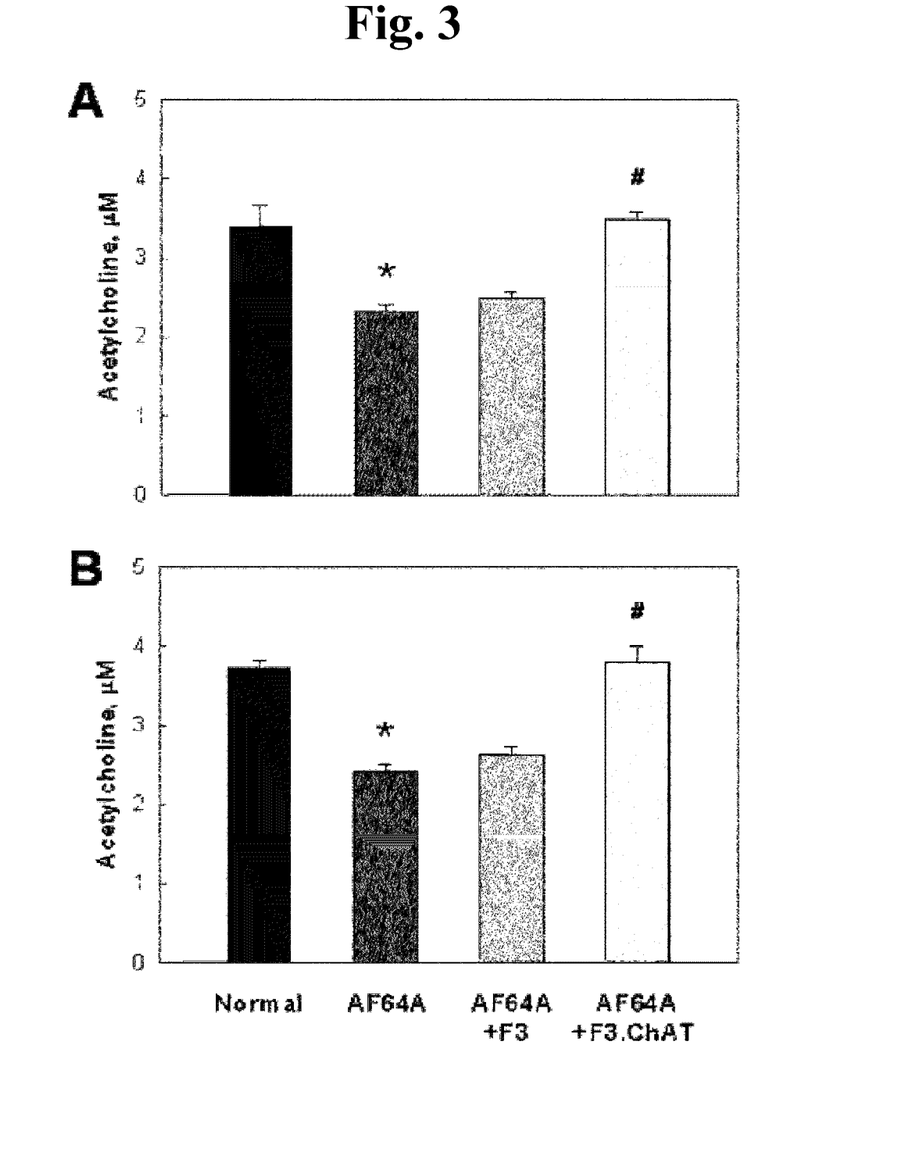
FIG. 3 shows the acetylcholine (ACh) concentration in rat cerebrospinal fluid (CSF) (panel A, 5 weeks; panel B, 9 weeks post-transplantation) post-transplantation of F3 or F3.ChAT cells ($1\times10^6$ cells/rat) following 2-week pretreatment with AF64A (3 nmol/rat). ACh concentration in CSF was measured with the Amplex Red acetylcholine/acetylcholinesterase assay kit (Molecular Probes). In this assay, ACh is hydrolyzed by AChE to release choline, which is then oxidized by choline oxidase to betaine and $H_2O_2$. $H_2O_2$ interacts with Amplex Red (7-dihydroxyphenoxazine) in the presence of horseradish peroxidase to generate the highly fluorescent resorufin. The resulting fluorescence was measured in a fluorescence microplate reader using excitation in the range of 530-560 nm and emission at ~590 nm.

Seven and 11 weeks after icy injection of cholinotoxin AF64A (3 nmol/rat), ACh concentration in CSF significantly decreased as compared with saline-administered control rats (FIGS. 3A and 3B). Such decreases in ACh levels were fully restored in AF64A brain receiving F3.ChAT cell transplantation 2 weeks after AF64A challenge, while in AF64A animals receiving control F3 cells ACh level remained low.

Because of the diffuse distribution of the transplanted NSCs, we analyzed ACh concentration in CSF rather than discrete brain regions. It is believed that mRNA expression (FIG. 1B) and protein production (FIG. 1D) of ChAT from F3.ChAT cells increased the ACh levels in CSF.

Example 13

Figure 4:
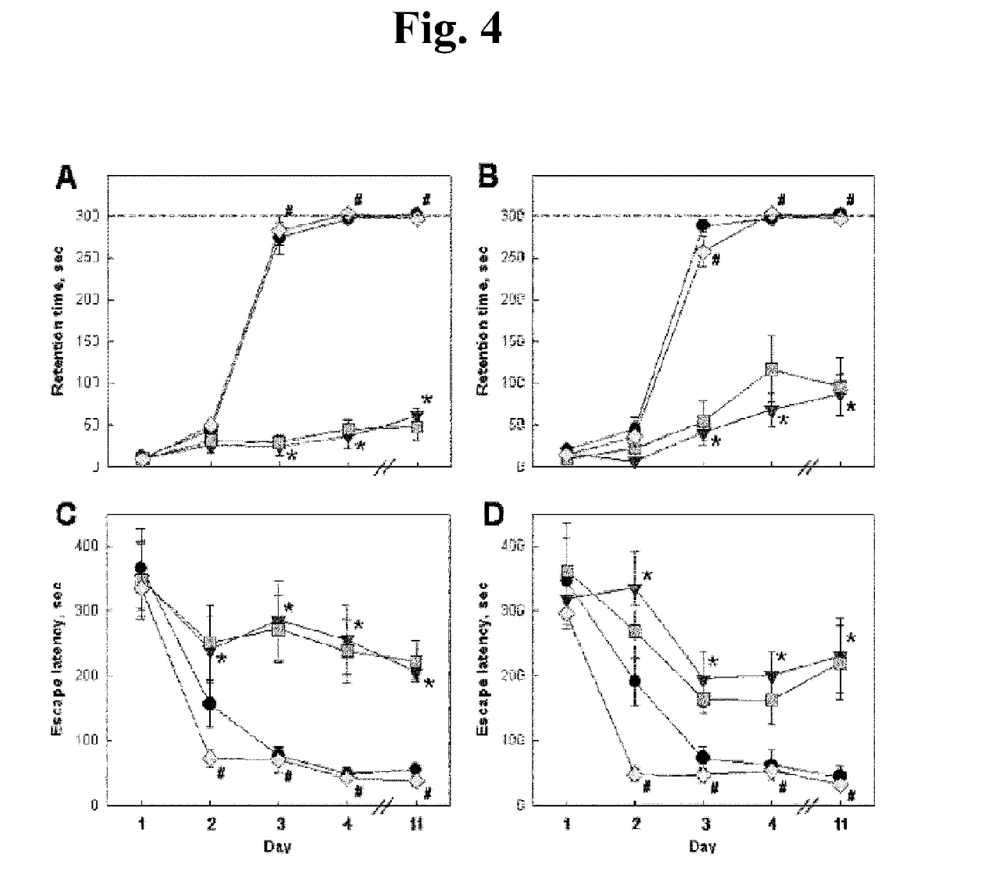
FIG. 4 shows the experimental results of the passive avoidance (panels A and B) and water-maze (panels C and D) performances 4-5 weeks (panels A and C) and 8-9 weeks (panels B and D) post-transplantation of F3 or F3.ChAT cells ($1\times10^6$ cells/rat) following 2-week pretreatment with AF64A (3 nmol/rat). ●, normal control; ▼, AF64A alone administration; ■, AF64A+F3; ◆, AF64A+F3.ChAT. On passive avoidance trials, electric shock (1 mA for 2 sec) was delivered when rats entered the dark compartment from the light room through a guillotine door. The latency time of stay in the light room from light-on was recorded. The end-point was set at 300 sec, denoting full acquisition of memory. On water-maze tests, rats were subjected to a performance consisted of 3 trials a day for 4 consecutive days, followed by 5th performance for further confirmation 1 week after the daily 4 performances at 4 or 8 weeks. The mean escape latency onto the platform was calculated.

Improvement of Learning and Memory Function in AD Animal by the Implantation of F3.ChAT Cells Rats challenged with AF64A (v) displayed severe impairment of learning and memory functions as measured by both passive avoidance (FIGS. 4A and 4B) and Morris water-maze (FIGS. 4C and 4D) performances 2 weeks (prior to cell transplantation, data not shown), 6-7 weeks (4-5 weeks after cell transplantation, FIGS. 4A and 4C) and 10-11 weeks (8-9 weeks after cell transplantation, FIGS. 4B and 4D) after AF64A injection as compared with normal rats (●).

Interestingly, AF64A rats receiving of F3.ChAT cells (♦) fully recovered the learning and memory functions at both 4-5 weeks and 8-9 weeks post-transplantation, whereas control F3 cells (■) were ineffective in doing so. [●, normal control; ▼, AF64A alone administration; ■, AF64A+F3; ♦, AF64A+F3.ChAT in FIG. 4]

Figure 2:
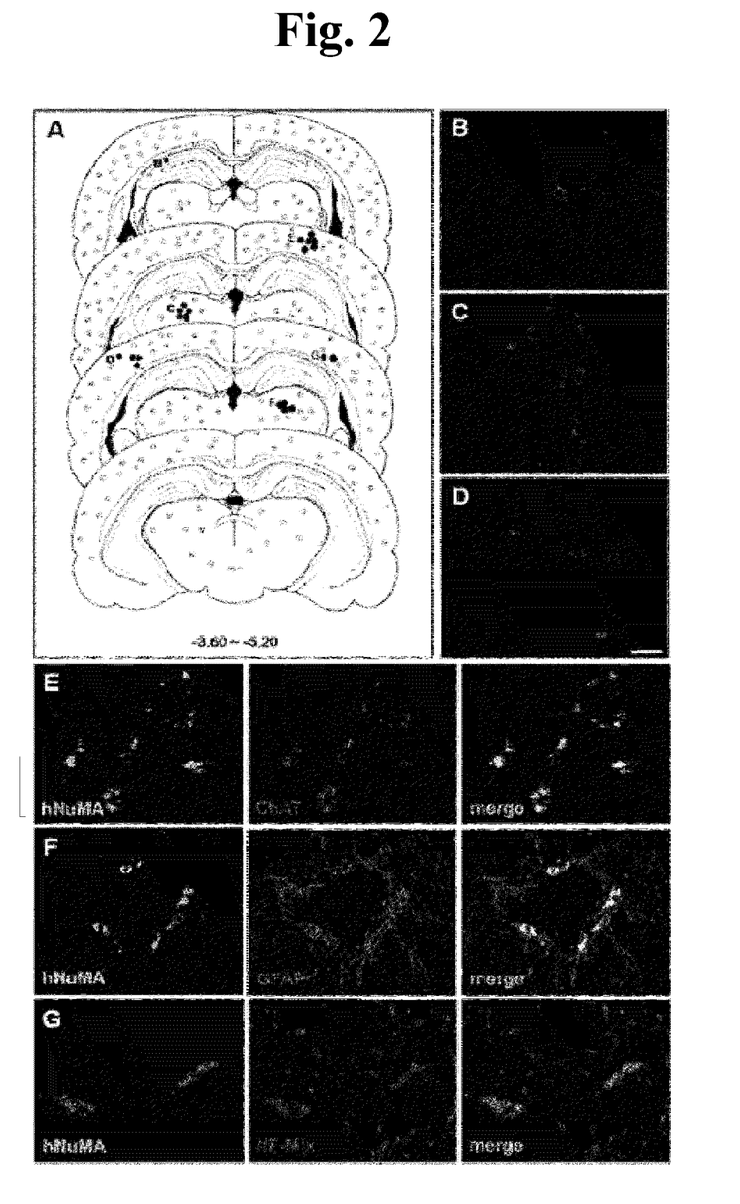
FIG. 2 shows the feature of the transplanted human F3.ChAT cells in the rat brain. Panels (A)-(D) represent the distribution of human F3.ChAT cells (identified by hNuMA-positive reaction) in the rat brain 9 weeks post-transplantation ($1\times10^6$ cells/rat) in AF64A-injected rats. Panel (E) shows the ChAT protein production in the rat brain 9 weeks post-transplantation ($1\times10^6$ cells/rat) in AF64A-injected rats. Panels (F) and (G) is the feature of the differentiation of the transplanted human F3.ChAT cells into astrocytes (GFAP-stained, F) and neurons (NF-Mix-stained, G) of human (hNuMA-stained) F3.ChAT cells 9 weeks post-transplantation. Scale bar, 50 μm.

As demonstrated in the above Example 12, transplantation of F3.ChAT cells ($1 \times 10^6$ cells/rat) fully restored the ACh level in the rat brain (FIG. 3). Thus, it is reasonably believed that learning and memory function of AF64A-treated rats were improved through the action of the implanted F3.ChAT cells and restored ACh level, comparable to normal animals (FIG. 4). By comparison, F3 parental cells slightly elevated CSF ACh content, but exerted a negligible effect on the memory function. F3 and F3.ChAT cells migrated to lesion sites, differentiated into neurons and astrocytes, and survived up to 9 weeks after transplantation (FIG. 2). We were unable to count the exact number of cells in brain sections, because of their diffuse and scattered distribution all over the brain. However, it was confirmed that most of the hNuMA-positive F3.ChAT cells expressed ChAT (FIG. 2), indicating that the transplanted F3.ChAT cells functioned in the new environment of host brain tissue, which was further supported by the increase ACh level in CSF (FIG. 3).

As shown in the present invention, the inventors demonstrated that the brain transplantation of human NSCs overexpressing ChAT in AF64A-induced AD model rats fully restored learning and memory function and ACh levels in the CSF, comparable to normal animal.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Terry, R. D. and Davies, P., Annu. Rev. Neurosci. 3, 77 (1980).
2. Whitehouse, P. J. et al., Science 215, 1237 (1982).
3. Coyle, T. J. et al., Science 219, 1184 (1983).
4. K. Kasa, P. et al., Prog. Neurobiol. 52, 511 (1997).
5. Terry, A. V. and Buccafusco, J. J., Pharmacol. Exp. Ther. 306, 821 (2003).
6. Musial, A. et al., Curr. Med. Chem. 14, 2654 (2007).
7. Goldman, S., Nat. Biotechnol. 7, 862 (2005).
8. Lindvall, O. and Kokaia, Z., Nature 441, 1094 (2006).
9. Kim, S. U. and deVellis, J. J., Neurosci. Res. 87, 2183 (2009).
10. Blurton-Jones, M. et al., Proc. Natl. Acad. Sci. USA 106, 13594 (2009).
11. Lee, H. J. et al., Stem Cells 25, 1204 (2007).
12. Lee, S. T. et al., Brain 131, 616 (2008).
13. Yasuhara, T. et al., J. Neurosci. 26, 12497 (2006).
14. Hwang, D. H. et al., Gene Ther. 16, 1034 (2009).
15. Fan, Q. I. and Hanin, I., Neurochem. Res. 24, 15 (1999).
16. Yamazaki, N. et al., Psychopharmacology (Berl.) 103, 215 (1991).
17. Bessho, T. et al., J. Neural Transm. 115, 1019 (2008).
18. Abe, E. et al., Br. J. Pharmacol. 108, 387 (1993).
19. Tsai, K.-J. et al., J. Exp. Med. 204, 1273 (2007).
20. Fisher, A. et al., J. Pharmacol. Exp. Ther. 222, 140 (1982).
21. Takashina, K. et al., J. Neural Transm. 115, 1027 (2008).
22. Shimato, S. et al., Gene Ther. 14, 1132 (2007).
23. Xuan, A. G. et al., Neurosci. Lett. 440, 331 (2008).
24. Wu, S. et al., Pathobiology 75, 186 (2008).
25. Srivastava, N. et al., Int. J. Dev. Neurosci. 27, 103 (2009).
26. Beck, K. D. et al., Nature 373, 339 (1995).
27. Schbitz, W. R. et al., Stroke 31, 2212 (2000).
28. Kim, S. U., Neuropathology 24, 159 (2004).
29. Matsuo, A. et al., Neurochem. Int. 46, 423 (2005).

What is claimed is:

1. A method for treating Alzheimer's disease, comprising: administering to a subject suffering from Alzheimer's disease, wherein the subject exhibits a decreased expression of acetylcholine, a therapeutically effective amount of a pharmaceutical composition comprising transfected HB1.F3 human neural stem cells (NSCs) in a manner that the transfected NSCs stably express human choline acetyltransferase (ChAT) in a brain tissue of the subject, wherein the transfected HB1.F3 human NSCs are transfected with a retroviral vector comprising a polynucleotide encoding human ChAT including the amino acid sequence of SEQ ID NO:1, a human cytomegalovirus (CMV) promoter which is operatively linked to the polynucleotide encoding human ChAT, and a SV40 polyadenylation signal sequence,
wherein the NSCs are immortalized by an introduction of a retroviral vector containing v-myc oncogene, and
wherein the method restores the acetylcholine level of the subject comparable to a normal acetylcholine level and improves learning and memory function of the subject when compared to a subject that was administered with non-transfected HB1.F3 NSCs.

2. The method of claim 1, wherein the retroviral vector comprising a polynucleotide encoding human ChAT is pLPCX.

3. The method of claim 1, wherein the method comprises administering about $1 \times 10^6$ NSCs.

4. The method of claim 1, wherein the pharmaceutical composition further comprises one or more pharmaceutically acceptable carriers selected from solvents, dispersion media, coatings, antibacterial and antifungal agents, and isotonic and absorption delaying agents.

5. The method of claim 1, wherein the pharmaceutical composition is administered by injection.

6. The method of claim 1, wherein the pharmaceutical composition is administered by intracerebroventricular administration.

* * * * *